US006649145B2

(12) United States Patent
McGrath et al.

(10) Patent No.: US 6,649,145 B2
(45) Date of Patent: Nov. 18, 2003

(54) COMPOSITIONS AND METHOD OF TISSUE SUPEROXYGENATION

(75) Inventors: Terrence S. McGrath, Boca Raton, FL (US); Charles Fox, Fair Lawn, FL (US)

(73) Assignee: Hydron Technologies, Inc.

( * ) Notice: Subject to any disclaimer, the term of this patent is extended or adjusted under 35 U.S.C. 154(b) by 105 days.

(21) Appl. No.: 10/052,075

(22) Filed: Jan. 18, 2002

(65) Prior Publication Data

US 2003/0083610 A1 May 1, 2003

Related U.S. Application Data

(60) Provisional application No. 60/265,819, filed on Feb. 1, 2001.

(51) Int. Cl.[7] .............................................. A61K 13/00
(52) U.S. Cl. ..................... 424/45; 424/400; 424/405; 424/434; 424/422; 424/484; 424/489
(58) Field of Search ........................ 424/45, 489, 422, 424/484, 400, 405, 434

(56) References Cited

U.S. PATENT DOCUMENTS

| 4,801,291 | A | 1/1989 | Loori |
| 5,006,352 | A | 4/1991 | Zelenak et al. |
| 5,029,579 | A | 7/1991 | Trammell |
| 5,154,697 | A | 10/1992 | Loori |
| 5,573,751 | A | 11/1996 | Quay |
| 5,766,490 | A | 6/1998 | Taylor et al. |
| 5,792,090 | A | 8/1998 | Ladin |
| 5,814,222 | A | 9/1998 | Zelenak et al. |
| 5,855,570 | A | 1/1999 | Scherson et al. |
| 5,869,538 | A | 2/1999 | Van Liew et al. |
| 6,248,087 | B1 | 6/2001 | Spears et al. |
| 2003/0021751 | A1 * | 1/2003 | Eckert .................. 424/9.52 |
| 2003/0083610 | A1 * | 5/2003 | McGrath et al. ........... 604/24 |

FOREIGN PATENT DOCUMENTS

CA 2299205 9/2000

OTHER PUBLICATIONS

Bowler PG.; Davies BJ., The microbiology of infected and noninfected leg ulcers, *International J Dermatology*, 38: 573–578, 1999.

Elden HR; Kalli T, Hydrogen peroxide emulsions, *DCI Magazine*, 157: 38, 40, 42, 44, 47, Aug. 1995.

Hopf HW, Hunt TK, West JM, et al. Wound tissue oxygen tension predicts the risk of wound infection in surgical patients. *Arch Surg* 132:997–1004, Sep. 1997.

Hunt TK, Rabkin J, Jensen JA, et al. Tissue oximetry: an interim report. *World J. Surg.*, 11:126–132, Apr. 1987.

Jonsson K. Jensen JA, Goodson WH, et al. Tissue oxygenation, anemia, and perfusion in relation to wound healing in surgical patients, *Ann. Surg,* 214:605–613, Nov. 1991.

Mellstrom A, Hartmann M, Jedlinska B, et al., Effect of hyperoxia and hypoxia on subcutaneous tissue gases and pH. *Eur. Surg Res* 31:333–339, Jan., 1999.

Hurley HJ, Permeability of the skin, in: *Dermatology, 3rd ed.*, Moschella SL, Hurley HJ, eds., W.B.Saunders; 1992.

Redkar R. Kalns J; Butler W et al., Identification of bacteria from a non–healing diabetic foot wound by 16 S rDNA sequencing, *Molecular and Cellular Probes* 14: 163–169, Jun. 2000.

(List continued on next page.)

*Primary Examiner*—Thurman K. Page
*Assistant Examiner*—Retford Berko
(74) *Attorney, Agent, or Firm*—Akerman Senterfitt; Stanley A. Kim

(57) ABSTRACT

Disclosed are methods and compositions for increasing tissue oxygen levels by administration of superoxygenated compositions of tissue surfaces. The methods are applicable to treatment of a wide variety of conditions including burns, bedsores, ulcers, necrosis and anaerobic infections.

31 Claims, 8 Drawing Sheets

OTHER PUBLICATIONS

Tegner E, Bjornberg A, Hydrogen peroxide cream for the prevention of white pressure areas in UVA sunbeds, *Acta Derm Venereol* 70:75–76, 1990.

Tyrrell JWG, Attard P, Images of nanobubbles on hydrophobic surfaces and their interactions. *Phys Rev Lett* 87(17):176104–1–4, Oct., 2001.

US FDA Medical Devices Advisory Committee, Meeting of: General and Plastic Surgery Devices Panel Closed Session, Nov. 17, 1998.

Whitney JD, Physiologic effects of tissue oxygenation on wound healing, *Heart and Lung* 18(5): 466–474, Sep., 1989.

* cited by examiner

COMPOSITIONS AND METHOD OF TISSUE SUPEROXYGENATION

This application is a continuation-in-part of provisional patent application Ser. No. 60/265,819 filed Feb. 1, 2001, the entire contents of which are hereby incorporated by reference.

1.0 BACKGROUND ART

1.1 Field of the Invention

The present invention is directed to oxygenating compositions and methods for administering high levels of oxygen to subcutaneous and subepithelial tissues. In particular, methods for surface delivery of super oxygenating compositions for such treatment are described.

1.2 Description of Related Art

In many medical conditions including diabetes, burns, bedsores, and wounds the ability to oxygenate tissue is compromised and arterial oxygen may not reach damaged skin. Tens of thousands of patients die each year in the U.S. as a result of complications from insufficient delivery of oxygen to compromised tissue. Poor oxygen delivery, particularly in the limbs, results in slow healing, infections, scar development, and in the worst cases, tissue death and amputation.

The effect of oxygen tension on wound healing has been extensively studied. (For a review, see Whitney, J. D. (1989)). Wound healing is dependent upon several processes including proliferation of fibroblasts, collagen synthesis, angiogenesis and re-epithelialization. Animal studies have shown that several of these processes are affected by the subcutaneous partial pressure of oxygen ($pO_2$). For example, supplemental oxygen can lead to increased rate of collagen deposition, epithelialization and improved healing of split thickness grafts. Increased subcutaneous $pO_2$ has also been shown to improve bacterial defenses.

Many skin sores, ulcers, wounds and burns do not heal properly because there is a severe depletion of oxygen reaching these affected areas due to deterioration of the associated blood microcirculation. Conventionally, many of these skin diseases have been treated by various methods of administration of oxygen gas, either through inhalation of the gas, or by topical treatment with the gas.

The oldest method of administering oxygen gas to a patient is by hyperbaric chamber technology. This is a systemic treatment, involving placement of a patient in a closed pressurized chamber. Inside the chamber, the patient breathes elevated levels of oxygen gas. The extra oxygen taken in by inhalation becomes dissolved in the bloodstream and diffuses into the body tissues, thereby raising the local tissue oxygen levels. Unfortunately, hyperbaric treatment has not been successful in all situations, in particular where trauma or disease restrict blood flow to the affected tissue. Treatment of skin diseases by placing a patient in a hyperbaric chamber is costly and time-consuming and many patients react unfavorably when placed in hyperbaric chambers. Treatment of many conditions, such as bedsores, for much longer than four hours at one time may induce oxygen toxemia and hence be counterproductive. Toxic effects of hyperbaric treatment include twitching, ringing in the ears, dizziness, and in some cases severe effects such as coma and convulsions. Additionally, hyperbaric treatment is expensive and only available in treatment facilities that are properly equipped with hyperbaric chambers. Patients are only given oxygen through the lungs. The atmosphere of a multichamber hyperbaric unit is ordinary atmospheric gas as there is little known therapeutic value assigned to topical application of oxygen.

To overcome drawbacks associated with systemic hyperbaric treatment, attempts have been made to use "topical hyperbaric" oxygenation devices designed for regional use on an isolated body part such as a limb. In such devices, the delivery route for the pressurized oxygen is topical, as opposed to systemic. Only the affected body part is exposed to the pressurized oxygen. Thus the oxygen gas must diffuse from the surface of the skin to the underlying tissues. For example, U.S. Pat. No. 4,801,291 discloses a portable topical hyperbaric apparatus having a gas impermeable internal chamber into which therapeutic gases are introduced to treat a portion of the patient's body. Similarly, U.S. Pat. No. 5,020,579 discloses a hyperbaric oxygenation apparatus in which a limb is isolated in a portable chamber in the form of an inflatable bag into which oxygen gas is administered through an oxygen port in communication with a patient respirator connected to an oxygen source. The pressure of the oxygen in the collapsible bag is pulsated between maximum and minimum positive values. The patient cyclically experiences first an increase in the blood gas levels on the limb under treatment with a corresponding restriction in blood flow and, thereafter, a progressive return to normal blood flow rates in the limb as the pressure in the chamber changes from maximum to minimum positive pressure.

Several disadvantages exist with the approach of using "topical hyperbaric" oxygenation devices. For example, an external oxygen source and a respirator normally used for respiratory therapy must be supplied with the apparatus. In addition, intermittent restriction and release of blood flow to the treatment area may not be advisable or tolerable for already compromised tissues.

Alternative topical methods to "topical hyperbaric" treatments for poorly healing skin lesions involve the topical application of high levels of oxygen gas through wound dressings. U.S. Pat. No. 5,792,090, discloses an oxygen generating wound dressing and a method of increasing oxygen tension in surface wounds through the application of such a bandage. In this method, the wound dressing contains an oxygen permeable membrane and a reservoir capable of supplying oxygen through a chemical reaction. U.S. Pat. No. 5,855,570 describes another type of oxygen-producing bandage to promote healing of skin wounds. This device combines a wound dressing with an electrochemical, chemical, or thermal means of generating high purity oxygen, and can be regulated to supply oxygen gas to an area above the wound at various concentrations, pressures and dosages.

Unfortunately, topical treatments with oxygen gas such as by topical hyperbaric oxygenation and use of oxygen bandages have provided only minor improvements in promoting healing of skin disorders and in treating diseases. Moreover, peroxide application can generate singlet oxygen $O_2$ and is a potential source of free radical damage to the skin (Elden, 1995).

1.3 DEFICIENCIES IN THE PRIOR ART

Administration of elevated levels of systemic oxygen gas has been recognized as beneficial in the treatment of several skin disorders; however, the available delivery methods, such as hyperbaric chamber therapy, topical application of oxygen gas, topical hyperbaric treatment of isolated limbs and use of oxygen-producing bandages are at best minimally effective and often lead to problems that include toxicity and poor oxygen penetration of the skin. Currently used procedures for treatment of skin disorders such as ulcers, bedsores, and burns may exacerbate the existing skin disorder.

It is therefore desirable to provide methods of treatment for skin disorders that increase tissue oxygenation to induce more rapid healing of the skin, while not exacerbating an existing condition or causing additional side effects.

2.0 SUMMARY OF THE INVENTION

Conventional methods of increasing tissue oxygenation employ oxygen gas. In distinct contrast, the present invention discloses a novel method of increasing tissue oxygenation by topical application of a superoxygenated composition. The superoxygenated compositions rapidly raise oxygen partial pressure levels in the tissue by promoting efficient diffusion of oxygen into the tissue.

Accordingly, the invention discloses a method of increasing tissue oxygenation in mammals, comprising applying a superoxygenated composition to a tissue surface for a time sufficient to increase the subepithelial partial oxygen pressure from about 30% to about 120% above baseline $pO_2$. The mammal will generally be a human, but there is no limitation to its use in veterinary applications to small and large animals that may have tissue damage responsive to therapeutic procedures that increase oxygenation of tissues.

The most common applications are direct application to the external skin but the method is equally applicable to mucous membrane surfaces of the alimentary canal as well as organ surfaces. Organs may be exposed or actually removed from the body cavity during surgical procedures. One may immerse an organ in a superoxygenated solution prepared in accordance with the invention, contact part of the organ with such a preparation, or perfuse the organ with the superoxygenated solution. In the latter case, this may be an ex vivo procedure intended to maintain organ viability and reduce ischemic damage.

One may desire to increase the oxygen level in tissues for several reasons, mainly in situations where the tissue is affected by a condition or disease such as bedsores, wounds, burns or ulcers or any condition that tends to decrease normal tissue oxygen levels. Additionally, It is expected to be particularly beneficial in treating anaerobic bacterial infections such as those caused by Pseudomonas species, Bacteroides species such as *Bacteroides fragilis, Prevotella melaninogenica, Prevotella bivia, Prevotella disiens,* Fusobacterium, Actinomyces, Lactobacillus, Propionibacterium, Eubacterium, Bifidobacterium, Arachnia, Peptostreptococcus, Veillonella, Clostridium species such as *C. tetani, C. botulinum, C. perfringens, C. difficile* and Porphyromonas. These infections may fester internally in lung tissue, oral or vaginal mucosa or become embedded in the surface of organs such as liver, kidney and heart.

Accordingly, one of the benefits of using the disclosed methods to enhance tissue oxygen levels is the toxicity to pathogenic anaerobic bacteria. A particularly desirable application is to control or kill the anaerobic bacteria responsible for peridontal disease. A superoxygenated mouthwash solution would be safe and convenient for use and can be packaged to maintain stability of the superoxygenated solution by using a pressurized container with means for single dose dispensing or packaged for single use.

The superoxygenated compositions of the present invention comprise at least about 55 ppm oxygen but find useful concentrations from about 45 to about 220 ppm. The oxygen level in the compositions depends on several factors, including the type of composition, the temperature, and other components, active or not, that may be added for various reasons such as stability, ease of application or to enhance absorption.

It is well known that gas concentration in fluids will be inversely proportional to the temperature. When desiring to use aqueous based superoxygenated compositions, the temperature will be dictated not by chemical considerations but by the potential damage to living tissue and by the need for higher oxygen concentrations. Accordingly, where the compositions are applied locally to external skin surfaces; for example to a forearm lesion, solution temperatures of about 0° C. will generally be considered appropriate. This will provide relatively high oxygen levels, typically in the range of 220 ppm. On the other hand, a patient may be whole-body immersed in a whirlpool bath at a more comfortable temperature in the range of about 34° C. The oxygen concentration will necessarily be less than 220 ppm due not only to temperature but also to the open environment commonly used in whirlpool baths in such establishments as rehabilitation centers.

The superoxygenated solutions and compositions of the present invention comprise oxygen microbubbles. Conventionally pressurized liquids such as carbonated beverages contain relatively large gas bubbles that escape fairly quickly into the atmosphere once pressure is released. The microbubbles employed in the disclosed compositions are much smaller, remain in solution longer and are thus more stable. Importantly, the oxygen provided by the microbubbles is at a partial pressure effective to quickly raise subepithelial oxygen partial pressure significantly above baseline or normal oxygen partial pressure levels.

As generated for use in the disclosed superoxygenated compositions, microbubble size is typically in the 1–2 micron range. The small size is believed to be an important contributor to the beneficial effects of topical application of solutions containing the microbubbles. The most preferred solutions appear to be those in which the oxygen bubbles are no larger than about 8 microns in size; however, a range of microbubble sizes exist in the prepared solutions, at least as small as 0.6 microns as detected at the limit of resolution by impedence methods for which results are illustrated graphically in FIG. 3. A practical range for many applications is between about $1\mu$ and about $1\mu$ in diameter or between about $3\mu$ and about $8\mu$ in diameter.

While the microbubble compositions need not be purely aqueous, compositions will normally comprise an aqueous base such as a buffer, or a pharmaceutically acceptable vehicle that will not be harmful if in contact with a tissue surface. Buffers, if employed, are preferably in the physiological pH range of 7.2–7.4 but may also be at lower pH such as provided by acetate buffers or at a higher pH in more alkaline buffers such as carbonate buffer. For many applications the superoxygenated compositions will comprise water and oxygen microbubbles.

It may be beneficial in some circumstances to provide agitation to the superoxygenated composition while it is being applied to the tissue. This will increase oxygen contact to the tissue surface and may increase efficiency of uptake. Agitation is inherent in the method of application when the compositions are part of a whirlpool bath treatment and may compensate somewhat for some decrease of oxygen in an open atmosphere environment and use of temperatures that are intended to provide patient comfort.

The oxygen supersaturated compositions of the invention may be applied in a variety of ways depending on the area to be applied, the nature of the condition and, for treatment purposes, the health condition of the subject or patient to be treated. Skin treatments will typically be applied as solutions that may be incorporated into creams, pastes, powders, ointments, lotions or gels or simply superoxygenated microbubble preparations in nonaqueous or aqueous media. An important consideration will be the concentration of microbubbles in the preparation and its ability to increase subepithelial partial oxygen pressure.

The method of application to the skin may be by soaking, immersion, spraying, rubbing or aerosols. The preparations may be applied to dressings that are in contact with the skin, such as plasters and wound coverings. In other applications, douches or enemas may be used for vaginal or rectal administration. Selection of the method will depend on particular patient needs, the area of application and type of equipment available for application.

Superoxygenated compositions are another aspect of the invention. The composition comprises an aqueous-based solution of oxygen microbubbles having a diameter of from about 0.6 micron to about 100 microns and having an oxygen concentration between about 45 ppm and about 220 ppm. Preferred embodiments include superoxygenated compositions where the microbubble diameter ranges from about 0.6 to about 5 microns and compositions where the microbubble diameter is about 5 to about 8 microns. A highly preferred superoxygenated composition includes microbubbles of oxygen in the range of 1–2 microns.

While liquid microbubble superoxygenated compositions will be preferred in most applications, the compositions may be in solid or frozen form. In aqueous based solutions this may be as low as −40° C. but could be as low as −70° C. in frozen gases such as carbon dioxide or in liquified gases such as nitrogen. These low temperatures are not practical for applications to living tissue; however, long term storage of certain cells or other biological material may benefit from this type of environment. In any event, there are several applications of superoxygenated aqueous solids in providing for example a slow release oxygen environment or where ice might be in contact with excised organs being transported for transplant purposes.

The compositions and methods disclosed may be combined in an apparatus for the purpose of providing a tissue oxygenating environment to a mammal in need of increased tissue oxygenation. An apparatus may include a container for holding an at least 55 ppm superoxygenated aqueous solution produced from an oxygen generating machine connected to the container. The apparatus may further include additional features for more efficient and convenient use, such as devices to agitate the superoxygenated composition being applied. In a particular embodiment, the device may induce a whirlpool effect. The device may be a sonicator to provide more effective distribution of microbubbles and which may help to maintain high oxygen levels in the solution. Stirrers, shakers, bubblers and the like may also be used to provide mixing.

The apparatus may also include a temperature controller that may be useful in controlling the oxygen levels in the superoxygenated solutions. An additional effect may be to enhance oxygen uptake through the skin of some subjects due to an increase in skin surface temperature. For use with patients, one may prefer to adjust temperatures to between about 37° C. and about 45° C.

In a particular application, the methods and compositions may be used to treat anaerobic infections. Generally this will involve applying any of the aforementioned compositions to a skin lesion suspected of harboring anaerobic bacteria. The method should be particularly effective against the anaerobic bacteria typically found in gangrenous or ulcerated tissue. Such anaerobic bacteria are also found in wound infections.

Patients are likely to benefit from increased tissue oxygen in the wound area. Burned skin areas are particularly susceptible to infection, particularly where tissue is destroyed or badly damaged as in second and third degree burns. Burn patients are expected to benefit from such treatment that can be used prophylactically as well as therapeutically. Other conditions that will benefit from increased tissue oxidation include the soft tissue in the oral cavity, particularly in treating gum disease that is usually caused by anaerobic bacteria.

For convenience, kits may be used to package various superoxygenated compositions prepared in accordance with the invention. An exemplary kit with appropriate instructions for use in topically increasing tissue oxygenation may contain a sealed permeable flexible container and a containerized superoxgenated composition in one or more of the variations described. The kits may additionally include a whirlpool generating device, and/or a thermostat/heating device for adjusting temperature inside the container.

As discussed, the disclosed methods employ application of a superoxygenated composition to a surface for a time sufficient to increase the subepithelial tissue partial oxygen pressure ($pO_2$) from about 30% to about 120% above baseline $pO_2$ levels. The method is applicable particularly to humans who suffer from such conditions as tissue necrosis, bedsores, ulcers, burns or anaerobic infection.

The present invention addresses several of the problems encountered in attempts to develop therapies and treatments that increase topical availability of oxygen to tissues, particularly to the skin. Skin conditions, such as ulcers, bedsores, wounds, burns, and other serious dermatological problems may be treated by utilizing an aqueous solution charged with oxygen microbubbles applied directly to the skin. An important application is scar reduction where treatment may be used subsequent to scarring or on wounds, burns or surgical incisions to reduce scar formation. The methods are also applicable to increasing oxygen levels in infected surface tissues such as puncture wounds and soft tissue infections of the oral cavity.

It is well known that many types of skin sores, ulcers, wounds and burns do not heal properly because there is a severe depletion of oxygen reaching these affected areas due to degeneration or damage of the associated blood microcirculation. The human skin is at the terminus of the oxygen delivery system and exhibits signs of oxygen loss in a variety of pathological conditions. Degeneration of skin tissue is largely due to oxygen deprivation. Although the skin is exposed to the atmosphere, only a negligible amount of oxygen is actually absorbed. Increasing the level of oxygen absorbed by the skin directly results in increased healing rates of the skin.

The present invention utilizes a method of tissue superoxygenation that provides oxygen to tissue to aid in its healing and revitalization. Oxygen is provided to the tissue through microscopic bubbles and is present at a pressure many times that found in blood. The oxygen in the microbubbles can be transported through the skin when placed in contact with the skin. Such treatment increases the oxygen level in the interstitial fluids of the subepithelial and dermal tissues and is immediately available to the oxygen-depleted cells, thereby inducing more rapid healing. The disclosed procedures will aid in the prevention of gangrene formation and treatment of sepsis, decrease the need for amputations in diabetic patients, and help to heal bedsores, skin lacerations, burns and wounds. This type of treatment is more convenient to use and is much more affordable than existing methods of treatment for these conditions, such as a hyperbaric chamber.

The methods are useful not only in prevention of several skin disorders but also in cosmetic and pharmaceutical applications. Of particular interest to many teenagers and even adults are formulations that will benefit healthy skin while also promoting healing of common acne, a skin condition that may be disfiguring to a certain degree.

Superoxygenated compositions may also benefit victims suffering from smoke inhalation and damage from inhaled hot air. In such cases, the disclosed superoxygenated compositions are administered directly to the lung in order to increase oxygen concentration to the damaged cells. Such treatment may also be used to wash inhaled particulates from the lungs and can be administered in conjunction with antibiotic and anti-inflammatory drug solutions where indicated. The superoxygenated fluid can be used as a spray or intubated as a soaking solution to provide more controlled contact with the internal surface of the lung.

In like manner, internal injuries such as bullet wounds may benefit from being flushed with the superoxygenated fluids herein disclosed. This will be particularly useful for deep wounds where surgery is not indicated or in field situations where access to the wound is difficult. In such cases, the wound is flushed with the disclosed compositions to inhibit anaerobic infection and to provide supplemental oxygen to damaged tissue.

The superoxygenated compositions are typically aqueous solutions of oxygen microbubbles with diameters from about 0.1 to about 10 microns, preferably about 1 to about 8 microns and more preferably at least about 0.6 to about 8 microns with oxygen concentrations from about 45 ppm to about 220 ppm. In most applications the solutions will include microbubbles with a range of sizes, including less than 0.6 microns up through 1,2,3,4,5,6,7,8,9 and 10 microns and may contain larger microbubble sizes as microbubbles coalesce, depending on temperature. Of course the oxygen concentration will depend on the temperature of the liquid, typical oxygen concentrations being up to about 220 ppm at 2° C. or about 118 ppm at 34° C. These concentrations may be varied depending on the condition of the tissue surface to be treated, the type of tissue and the location of the tissue surface.

In special applications considerably higher oxygen concentrations may be desired; for example, well above 220 ppm. This may be achieved by preparing solutions of oxygen nanobubbles as small as 20–30 nanometers such as those described in association with flowing liquids across hydrophobic surfaces (Tyrrell and Attard, 2001). Nanobubbles are thought to be flat rather than round and to form closely packed, irregular networks that nearly completely cover hydrophobic surfaces. They appear to reform quickly after being distributed and are therefore quite stable. Regardless of how nanobubbles are produced, it is likely that concentrations of oxygen significantly higher than 250 ppm may be attained and will be useful in achieving high tissue oxygenation levels.

Oxygen microbubbles may be prepared in water or in a pharmaceutically acceptable vehicle. Physiological saline, various buffers, or compounds that increase wetting and porosity are examples of composition variations. In some cases, one may wish to add antibiotics, anti-inflammatory compounds or other drugs to the compositions in order to expedite healing or more effectively treat certain bacterial infections.

In certain applications, it may be desirable to administer superoxygenated compositions in the form of creams, lotions, gels or solids. Such formulations are well recognized and accessible to those skilled in the art. The superoxygenated compositions may also be maintained in a frozen state, for example for storage, or for use in treatments where ice can be conveniently applied to a tissue surface so that higher levels of oxygen can be consistently maintained. In a particularly important application, frozen or chilled superoxygenated compositions may be used for storage and transport of organs intended for transplantation. This may avoid or ameliorate anoxic conditions arising from severance of the organs from the normal blood supply. Frozen or chilled compositions will be especially beneficial for such tissues, both because enzymatic processes are retarded at the lower the temperature, and because at lower temperatures, higher levels of oxygen can be incorporated into the oxygenated compositions so that degradation is inhibited.

The superoxygenated compositions may be administered in several ways such as through tubes connected to flexible bags containing superoxygenated solution or in some applications by immersion of tissue in a bath containing the oxygenated solution. For dental applications in treating gum disease, administration by a device similar to a water pic is an effective method for topically administering suitable superoxygenated solutions. Certain applications benefit from mixing or agitating procedures so that fresh solution constantly bathes the tissue; for example, lavage procedures or whirlpool baths in which an affected limb is immersed.

In certain embodiments, an apparatus for providing a tissue oxygenating environment to a mammal in need of increased tissue oxygenation is also within the scope of the invention. Such an apparatus incorporates a machine for generating oxygen microbubbles that may be as simple as an oxygen cylinder connected to a pressurized vessel at pressures in the range of 90–110 psi and introducing oxygen gas into the vessel that holds a liquid such as water or other suitable water-based fluid. An oxygenator may also be used, generating about 50 psi. A tube or other exit from the vessel provides the oxygenated solution to the target tissue. Oxygen levels in the solution may be increased by agitating or sonicating the vessel. Ultrasonic equipment external to the flow intake and adaptations to control diffusion patterns in a vessel or a bath may also be employed.

It will be appreciated also that solution temperature will affect total oxygen concentration so that in alternative embodiments, the apparatus may incorporate any of a number of well known devices for controlling temperature such as thermostatted baths. Thus where applications are whole limb or body applications in open air as in a whirlpool bath, oxygen concentrations will not usually exceed about 55 ppm. For treatment of an internal epithelial lining, as in oral mucosal infections, cooler temperatures and correspondingly higher oxygen concentrations will be tolerable. Oxygen concentrations will vary depending on the method of application whether by soaking, immersion, spraying, rubbing or aerosols; however, in any event, the compositions contacting the affected tissue will have a significantly increased oxygen concentration in the range of at least about 45 ppm.

While most applications will utilize aqueous solutions, the inventors do not wish to be unduly limited since high oxygen concentrations may be achieved in nonaqueous or aqueous/organic solvents. Such solvents should be non-toxic and pharmacologically acceptable for human use. Perfluorocarbons are a particular example of non-aqueous solvents that might be useful. Other solvents include those that are water-miscible such as alcohols and glycols. In certain applications it may be convenient to use gel formulations such as hydrophilic gels formulated from alginates or carrageenans.

Other embodiments include kits that conveniently provide some form of the apparatus described above and will be useful for topically increasing tissue oxygenation. Exemplary kits may include a sealed permeable flexible container containing a superoxygenated composition and instructions for applying the composition to the tissue surface or skin requiring increased oxygenation. Optional kit components include a thermostat/heating device for adjusting temperature inside the container and an oxygen supply connectable with a pressurized vessel for mixing, agitating or sonicating an oxygenated fluid.

3.0 BRIEF DESCRIPTION OF THE DRAWINGS

The drawings form part of the present specification and are included to further demonstrate certain aspects of the present invention. The invention may be better understood by reference to one or more of the following drawings in combination with the detailed description of specific embodiments presented herein:

4.0 DETAILED DESCRIPTION OF ILLUSTRATIVE EMBODIMENTS

There is a need for improved treatments for skin disorders such as gangrene, skin ulcers, bedsores, burns, and other serious dermatological problems. The present invention utilizes the application of a highly oxygenated product in the treatment of several skin disorders. The disclosed highly oxygenated products will be useful in treatment of skin diseases related to degeneration of skin tissue due to oxygen deprivation, such as ulcers, burns and skin wounds.

4.1 Oxygen Release to Cells

Figure 1:
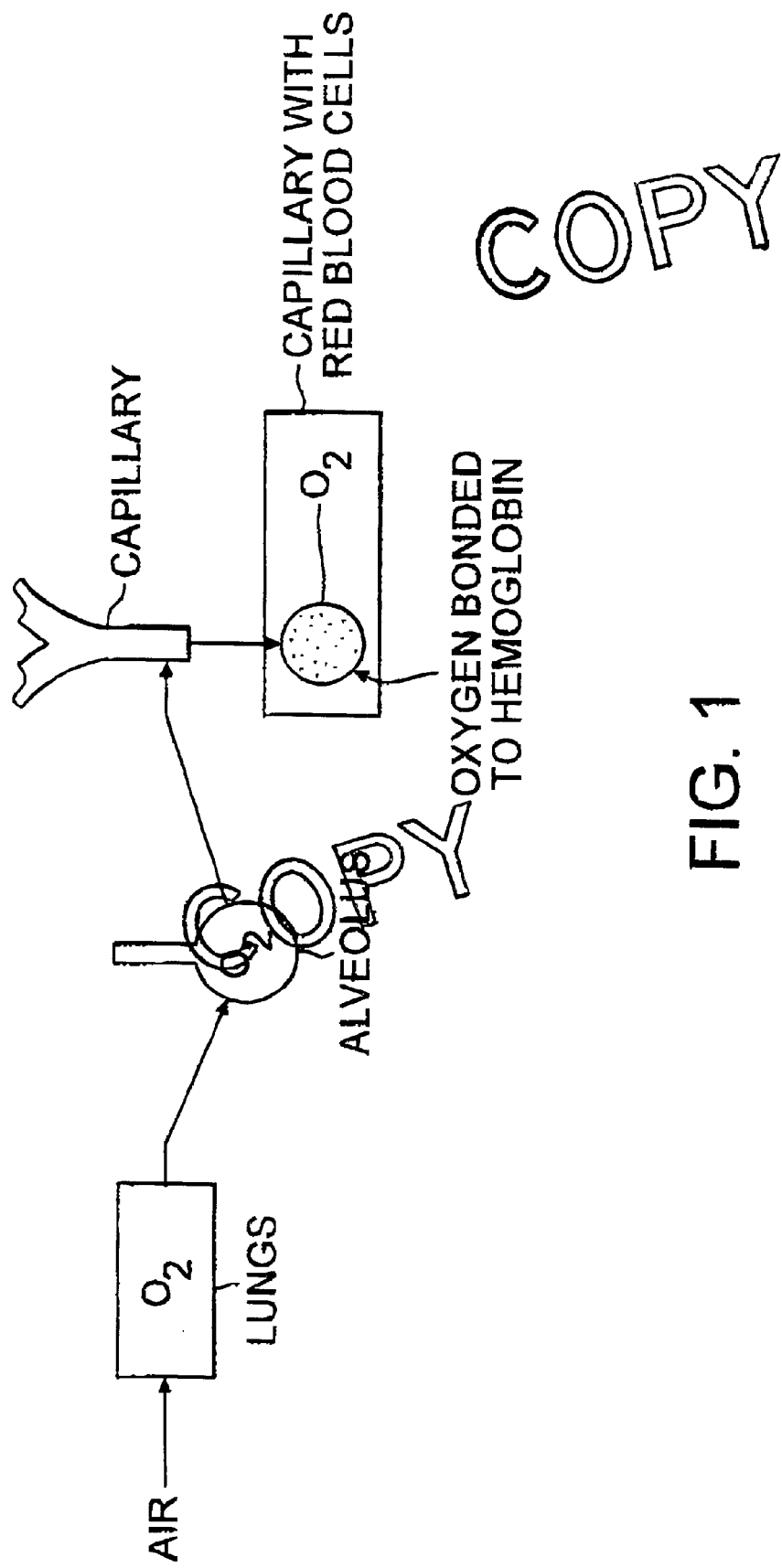
FIG. 1 Illustrates oxygen release to cells

As shown in FIG. 1, oxygen is transported from the air into the body. Air, which contains approximately 20% oxygen, passes upon inhalation into the bronchial tubes and ultimately into the alveoli of the lungs. In the alveoli, oxygen diffuses across very thin capillary walls to enter the bloodstream, where it combines with hemoglobin in the red blood cells to form oxyhemoglobin. As the blood circulates through the body, oxygen is released from the oxyhemoglobin and diffuses into the tissues and cells of the body, including the skin.

Gases are usually measured in terms of pressure. Air is a mixed gas and is measured in terms of absolute and partial pressure. For example, at sea level air has an atmospheric pressure of 760 mm of mercury (Hg), meaning that it will support a column of mercury 760 mm high in a tube 1 mm in diameter. Oxygen makes up 20% of the gases in air; thus the partial pressure of oxygen ($pO_2$) is 20% of 760, or 152 mm Hg. At higher altitudes, the $pO_2$ of air is decreased. In the lungs, the partial pressure of oxygen is 100 mm Hg.

Figure 2B:
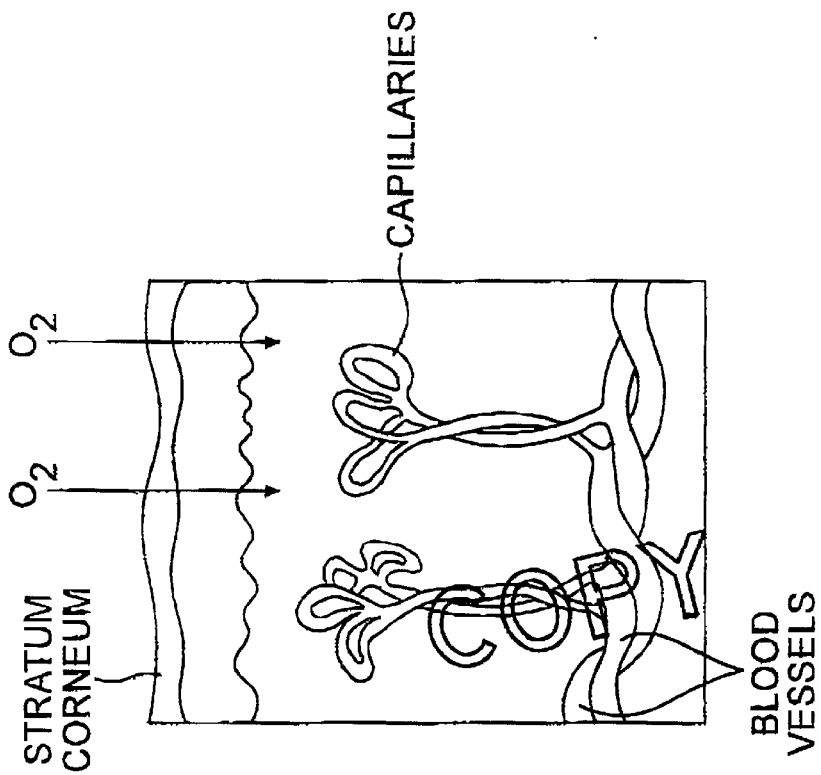
FIG. 2B Illustrates a cross-sectional view of abnormal skin. The superoxygenated composition of the invention is applied to the surface of the skin; arrows indicate direction of movement of oxygen through the epidermis and into the underlying subcutaneous tissues.
Figure 2A:
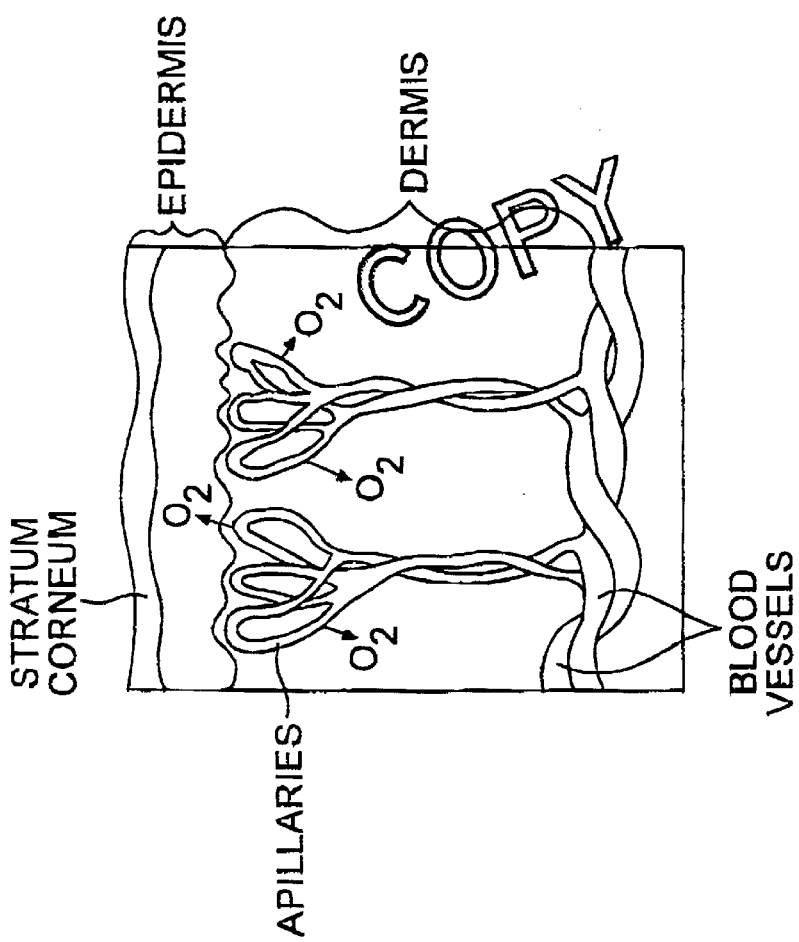
FIG. 2A Illustrates a cross-sectional view of normal skin. Arrows show normal direction of diffusion of oxygen from capillaries into dermis and overlying epidermis.

The diffusion of oxygen into cells and tissues depends on the partial pressure of oxygen, the solubility of oxygen in the body fluids and on the health of the tissue. Oxygen does not penetrate the skin at atmospheric pressure, but only interacts with the outer surface. Thus under normal conditions, the skin is nourished not from oxygen in the air, but from $O_2$ that diffuses from beneath into the deep, living layers of the epidermis and the underlying dermis from capillaries in the dermis (FIG. 2A). Compromise to the blood supply of the skin through damage or disease thus severely affects the ability of the damaged skin to obtain an adequate oxygen supply.

Hyperbaric oxygen therapy is a systemic treatment to increase tissue oxygenation involving administration of oxygen at pressures higher than atmospheric pressure. This requires the use of a special chamber to contain the high pressure (usually between 2 and 3 times atmospheric) which is needed to force extra oxygen to dissolve in the plasma, which in turn forces it into the tissues. To date, the majority of skin conditions resulting from lack of oxygen are treated with systemic hyperbaric methods and nonoxygenated topical applications. For example, the hyperbaric oxygen chamber has been established as the primary therapy in the treatment of medical disorders such as Clostridial Myonecrosis (Gas Gangrene). On average, treatments usually last from 1 to 2 hours at full pressure, which may be problematic because extended exposure to hyperbaric treatment at these pressures produces high risks of toxicity.

Hyperbaric oxygen therapy is also used to treat bedsores. Skin has a rich blood supply that delivers oxygen to all its layers. If that blood supply is cut off for more than two or three hours, the skin begins to die, beginning at its outer layer, the epidermis. A common cause of reduced blood flow to the skin is pressure. Normal movement shifts pressure and enables the continuous movement of the blood supply. Once a person is limited in movement or bedridden they are at a high risk for developing bedsores. Bedsores can further develop into decubitus ulcers. These ulcers can open skin to the bone, causing a great deal of pain and can result in a life-threatening situation.

In some cases, "topical hyperbaric" treatment for bedsores, involving exposure of an isolated portion of the body to oxygen gas, is claimed to be effective during the early stages of infection There is concern with this method that there is lack of penetration of the topically applied oxygen, largely due to the difference in the pressure under the surface of skin and the atmosphere (FDA Advisory Meeting, Nov. 17, 1998). Also oxygen delivery topically causes a burning effect on the surface of a skin after continuous application to skin.

In the present invention, a method of tissue oxygenation using superoxygenating compounds has been developed to treat dermatological problems by inducing more rapid healing. The tissue is provided with oxygen by a method utilizing topical application of highly oxygenated water or other fluid incorporating microscopic oxygen bubbles. When applied for example to skin, the oxygen is transported inward from the surface through the deeper layers of the skin (FIG. 2B), thereby providing oxygen to the cells of the epidermis and underlying dermis. The highly oxygenated solutions will increase the level of oxygen in the subcutaneous and subepithelial tissues and promote healing by providing oxygen to oxygen-depleted cells.

5.0 EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Materials and Methods

Superoxygenated solutions were prepared according to processes for enriching a liquid with oxygen by introducing the liquid into an oxygen enriching vessel similar to the disclosure of U.S. Pat. No. 5,006,352, hereby incorporated by reference. Briefly, the oxygenation process is carried out in an oxygen enriching apparatus as disclosed in U.S. Pat. Nos. 5,766,490 and 5,814,222, herein incorporated by reference in their entirety.

The process utilized by the inventors introduces a liquid into a closed space or pressurized vessel, mixes the liquid with oxygen in a turbulent mixer and recovers an oxygen-enriched liquid with an oxygen content of at least 40 mg/l oxygen. A superoxygenated fluid having an oxygen concentration of 180–217 ppm was prepared using distilled water. This solution contained oxygen microbubbles with diameters averaging about 1 micron and usually in the range of 0.6–8 microns, as measured using a flow impedence device. For measurement of bubble diameters oxygenated water samples were dispersed by mixing equal amounts of each with Isoton II in 20 ml cuvettes. Analyses were performed with a 30 μm aperture tube using Time-mode for 30 seconds. Table 1 summarizes results showing that the mean size of the oxygen bubbles was in the range of 1 μm. Attempts to measure particle size using a laser diffraction instrument were unsuccessful.

TABLE 1

| | Particle Size | |
|---|---|---|
| SAMPLE | VOLUME MEAN SIZE (μm) | NUMBER MEAN SIZE (μm) |
| 119–155 | 6.29 | 1.30 |
| 107–123 | 2.21 | 1.07 |
| 180–216 | 9.31 | 1.11 |

Figure 3:
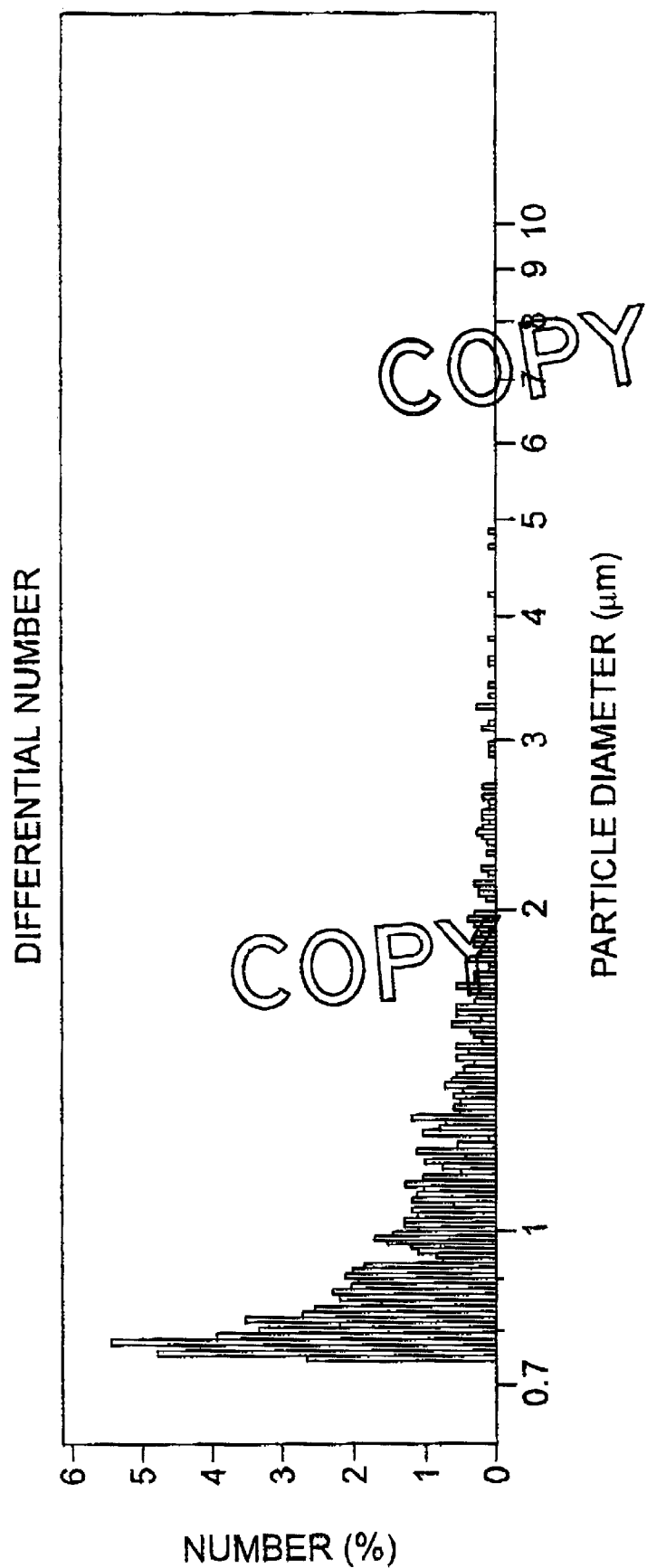
FIG. 3 Shows the size distribution of microbubbles in the superoxygenated composition.

Distribution of particle size in a typical sample is represented in FIG. 3. The graph shows particle distribution in terms of solution volume, indicating that in the sample 90% of the particles were 1–2 μm in diameter.

5.1 Example 1

Increase in Subcutaneous Oxygen in Porcine Skin

This example demonstrates that a solution containing superoxygenated microbubbles, applied topically to the skin of a pig, increases the level of oxygen in the underlying subcutaneous tissue.

The skin was cleaned with alcohol, hydrogen peroxide and then water. Arterial blood gas monitoring devices ("sensors") capable of simultaneous measurement of partial pressure of carbon dioxide ($pCO_2$), temperature and pH were inserted 1–4 mm beneath the skin surface, on the left and right sides of the body. Containers for test solutions, such as flexible bags with tubes at one end, were affixed with adhesive to the skin surrounding the sensor. The containers provided a means of immersing the skin under a column of test or control solution during the test. Prior to filling the containers, controls established that the choice of adhesive (Fixodent® or Stromahesive paste) had no effect on the baseline $pO_2$ reading.

The sensors were allowed to equilibrate for 30 minutes and both were stable before the interventions were begun. Control and test solutions were heated to 34° C., and equal volumes were added to the container to ensure equal pressure on the skin site during measurement. Control solution was distilled water (approx. 7–9 ppm $O_2$) and the test solution was superoxygenated water having an $O_2$ content of 180–217 ppm.

Figure 4:
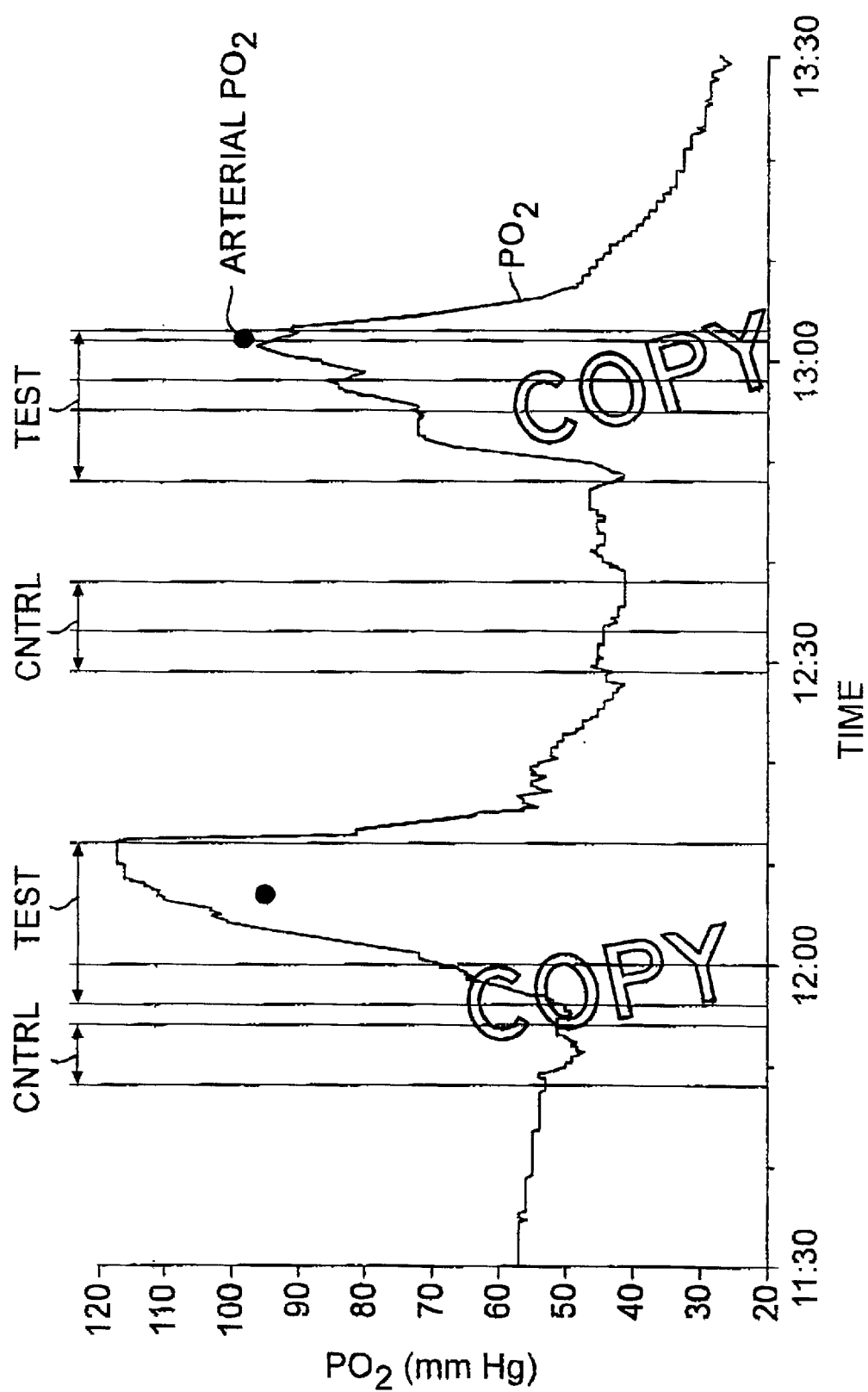
FIG. 4 Shows measurements of subcutaneous $pO_2$ levels in pig skin, indicating rapid diffusion of oxygen through the skin following topical application of oxygen microbubbles. Topical application of control solution had no effect.

As shown in FIG. 4, at the start of testing, baseline $pO_2$ was 55 mm Hg in the sensor positioned at the test site on the left side. The control solution was placed in the container for 6 min, during which interval no increase in $pO_2$ was seen (FIG. 4). The control solution was removed and test solution was placed in the container at t1 and again four minutes later (second dotted line). Addition of the test solution resulted in an increase in $pO_2$ from 54 to 117 mm Hg. This tissue level was 23% higher than the arterial $pO_2$ value of 95 mm Hg. (FIG. 4). As soon as the test solution was removed by suction, the $pO_2$ returned to baseline.

The cycle was then repeated. Control solution was placed in the container thirty minutes later (12:30) and more was added to keep the skin surface covered. No increase in $pO_2$ was observed. Subsequently, the control solution was removed and replaced with several additions of test solution (dotted lines). With additions of test solution, there were peaks in $pO_2$ levels (FIG. 4).

Figure 5:
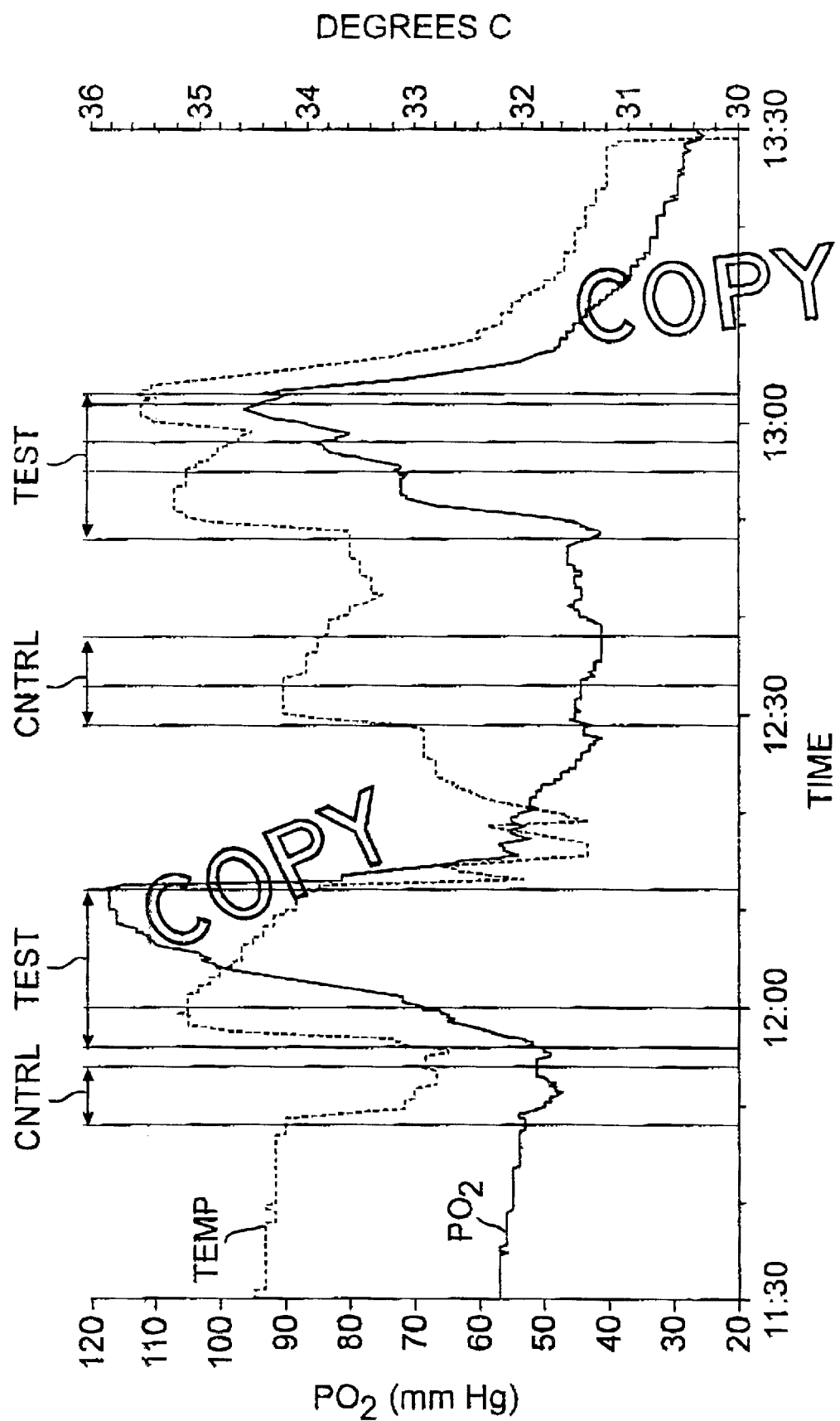
FIG. 5 Shows comparison of $pO_2$ increase and skin temperature, indicating increase in $pO_2$ following topical application of oxygen microbubbles alone, with comparable skin temperatures following application of test or control solution.

Sensor response is known to be affected by temperature. It was important to determine the relationship between the $pO_2$ increases and the skin temperature at the test site. As seen in FIG. 5, both the control and test solutions altered the skin temperature by 1–2° C. Because the $pO_2$ increased only with the superoxygenated test solution, it was concluded that the increases in $pO_2$ were not due to changes in temperature but were actually due to the application of the test solution to the surface of the skin.

A second test using the sensor implanted on the right side of the animal revealed the importance of the placement of the electrode. Differences were not observed between the $pO_2$ levels recorded with control and test solutions. However, the baseline $pO_2$ at the site was 75 mm Hg, much closer to the blood $pO_2$ level of 90 mm Hg, (as compared with 55 mm Hg on the left side site). This may have been due to the sensor being in close proximity to a capillary. Gas exchange from the blood may have caused the differential between the flowing blood and the test solution to be too small to observe. Alternatively, the sensor may have been placed too deep to detect diffusion of $O_2$ through the skin.

5.2 Example 2

Increase in Subcutaneous Oxygenation in Human Subjects

Results from procedures with human subjects demonstrated that oxygen in superoxygenated solutions prepared as described can be delivered to subcutaneous tissue through healthy human skin to increase subcutaneous $pO_2$ above baseline levels.

After receiving informed consent from ten human subjects, baseline blood pressure and heart rate were measured. A pulse oximeter probe was placed on the subject's finger for continuous monitoring of heart rate and oxygen saturation throughout the study. The skin over the outside of the left calf was disinfected with betadine and the betadine cleaned from the surface of the skin. A catheter (22 Ga, 1 ⅜" catheter, Product No. 04122, Arrow) was surgically inserted in under the surface of the skin and then out, so the tip of the needle and catheter were exposed and almost the entire length of the catheter was in the subcutaneous space. The catheter was placed as close to the surface of the skin as possible without driving the needle through the skin prematurely, in order to place the catheter in the dermis or at the border of the dermis and subcutaneous tissue.

After the catheter was placed, the needle was removed and the tip of the sensor was lined up with the tip of the catheter. The sensor was advanced through the catheter using the sensor advancement mechanism until it was visible from the other end of the catheter. The catheter was removed and the sensor was drawn back until the tip of the sensor just disappeared beneath the skin. The sensing element was 2.5 cm long and was completely contained beneath the skin. The holes made by the catheter were covered by a water resistant dressing (Duoderm® thin, Product number NDC 0003-1879-55, ConvaTec) and the sensor housing was taped in place to keep the weight of the housing and cable from pulling the sensor out.

The skin around the sensor was prepped with a barrier wipe (Allkare®, ConvaTec). Stoma paste (Stomahesive, Product number NDC 0003-1839-10 ConvaTec) was placed on the skin where the flexible bag (ActiveLife®, Product number NDC 0003-0254-33, ConvaTech), with a 2.5" hole, was to be placed. The bag was then placed on the applied paste. Any gaps between the bag and the skin, particularly around the sensor housing, were filled with stoma paste. The bag was also sealed to the skin with Hytape around the sensor housing.

Tests were performed in two phases, the first phase involving testing of responses to control and oxygenated solutions applied over the sensor sites by means of attached bags, as in Example 1. The second phase, carried out after the first on the same patients, involved removal of the bag while maintaining the sensor in place, to enable subsequent testing of responses when the legs of the subjects were immersed in test solutions in a whirlpool bath. The whirlpool bath was a standard stainless steel bath approximately 30" long×18" wide×30" high of the sort typically used for physical therapy and in other clinical settings.

In phase one, two different concentrations of oxygenated water and a control solution in the bag. The oxygenated water for this test was prepared as previously described. The sensor was allowed to equilibrate for 30 minutes after insertion. The sensor simultaneously measured and recorded temperature, partial pressure of oxygen ($pO_2$), carbon dioxide ($pCO_2$) and pH. Data were collected every 10 seconds on a laptop computer throughout the entire study. Individual bottles containing these solutions were heated to 32° C. (except for a few subjects; see Table 2). The order of these solutions was randomized. 500 ml of the selected solution was placed in the flexible bag, which was then closed with the clip. The solution remained in contact with the skin for 15 minutes. A 15 minute stabilization period was maintained between each solution. Not all subjects received 3 solutions (see Table 2). At the completion of this phase the bag was cut from the adhesive frame to expose the skin-covered sensor to air and eventually to water in the whirlpool.

For the second (whirlpool) phase, the procedure for producing the oxygenated solutions was modified as follows. Oxygen is known to dissipate rapidly from solutions in open vessels. In order to continuously maintain elevated oxygen levels in the solutions as the solution circulated in the open bath, the outflow from the bath was connected to the inlet of the oxygenation machine, which allowed for recirculation at a rate of 35 gal/min, and return of all of the water to the bath every 2 minutes. Both control and oxygenated solutions were subjected to pressures of 90 psi within the machine, and continuously circulated throughout the tests. Oxygenation of the circulating water was achieved rapidly after activating the oxygen input in the machine, and the level of $O_2$ was monitored throughout the test by a dissolved oxygen meter in the bath. The presence of the oxygen in the water was also detected visibly by the change in its appearance to a milky white solution.

The tape covering the sensor was removed and the bag adhesive pulled back part way. The sensor was withdrawn from the skin using the sensor retraction mechanism. The subject's blood pressure and heart rate were measured at the end of the study. In three of the subjects the thickness of the dermis and depth of the sensors were measured using a 20 MHz ultrasound system from GWB International.

At the beginning of this period the sensors had been in the tissue at least 1 hour. When the leg was inserted into the heated whirlpool the temperature quickly (within <1 min) rose to the level of the bath. The baseline readings for temperature, $pO_2$, pH and $pCO_2$ were recorded just at the time the temperature stabilized to the bath level. Control readings and subcutaneous oxygenation readings were taken at the end of the period for each subject. Statistical analysis was performed on the data collected during the whirlpool phase. Changes in temperature and subcutaneous $pO_2$ between baseline, control and oxygenation periods were compared with a repeated-measures Anova test, followed by a Tukey HSD test to elucidate differences between the time periods.

Five male and five female subjects were tested in this study. Table 2 details the specific characteristics of each of the subjects and the protocol. All subjects would be considered overweight (BMI 25). Subjects received slightly different treatment before the whirlpool study. However every subject had at least 1 hour sensor stabilization time before the whirlpool study began and every subject spent approximately 30 minutes in the oxygenated water. All statistical analysis was limited to the time period in the whirlpool.

TABLE 2

Subject characteristics and specific protocols

| Subject | Gender | Age | BMI | test soln 1 (15 m) | test soln 2 (15 m) | test soln 3 (15 m) | total time before whirlpool (m) | whirlpool cntrl (m) ~4 ppm | whirlpool O2 (m) ~55 ppm | Temp (C.) |
|---|---|---|---|---|---|---|---|---|---|---|
| HY01 | F | 41 | 35.1 | 4 ppm | 4 ppm | 112 ppm | 109 | 11 | 24 | 32 |
| HY02 | F | 42 | 31.1 | 120 ppm | 115 ppm | 4 ppm | 105 | 16 | 34 | 32 |
| HY03 | M | 43 | 26.5 | 101 ppm | 4 ppm | | 90 | 17 | 30 | 32 |
| HY04 | M | 46 | 25.8 | 131 ppm | 118 ppm | 4 ppm | 121 | 16 | 33 | 32 |

TABLE 2-continued

Subject characteristics and specific protocols

| Subject | Gender | Age | BMI | test soln 1 (15 m) | test soln 2 (15 m) | test soln 3 (15 m) | total time before whirlpool (m) | whirlpool cntrl (m) ~4 ppm | whirlpool O2 (m) ~55 ppm | Temp (C.) |
|---|---|---|---|---|---|---|---|---|---|---|
| HY05 | F | 41 | 34.0 | 116 ppm | 4 ppm | 120 ppm | 127 | 15 | 36 | 32 |
| HY06 | M | 53 | 27.0 | 134 ppm | 4 ppm | | 92 | 30 | 30 | 32 |
| HY07 | F | 54 | 30.1 | 111 ppm | 4 ppm | | 92 | 30 | 33 | 34 |
| HY08 | M | 41 | 31.9 | 131 ppm | | | 60 | 30 | 34 | 35 |
| HY09 | F | 44 | 33.6 | 150 ppm | | | 61 | 30 | 26 | 37 |
| HY10 | M | 40 | 33.0 | 130 ppm | | | 60 | 30 | 33 | 34 |

Table 3 details a qualitative assessment of the sensor depth, with quantitative measurements for the 3 subjects with studied with ultrasound. Based on the ultrasound measurements, if the sensor could be felt as a bulge through the skin, it is likely that the sensor was at the interface between the dermis and underlying subcutaneous tissue. In one subject (HY03), the sensor came out because it failed to be locked in place. This subject had the sensor re-inserted in the same region of tissue. Another subject (HY09) had bleeding when the sensor was inserted and a blue line of blood was observed under the skin, along the sensor, suggesting that this sensor may have been sitting in blood. In a third subject (HY10) there was bleeding when the sensor was removed, suggesting that there may have been blood in the channel for this subject as well.

For the whirlpool phase of the testing, the bath was heated to 32° C. (except for a few subjects, see Table 4). For the first 5 subjects, the leg was immersed in the bath in control solution (distilled water at 4 ppm $O_2$) for 15 minutes. For the last 5 subjects, the control phase lasted 30 minutes. After the control period, the oxygenation machine was turned on to oxygenate the water. Full oxygenation (~55 ppm) was reached in 3–4 minutes and the leg was immersed for 30 minutes in oxygenated water. The subject's leg was then removed from the bath and followed for 15 minutes.

Figure 6:
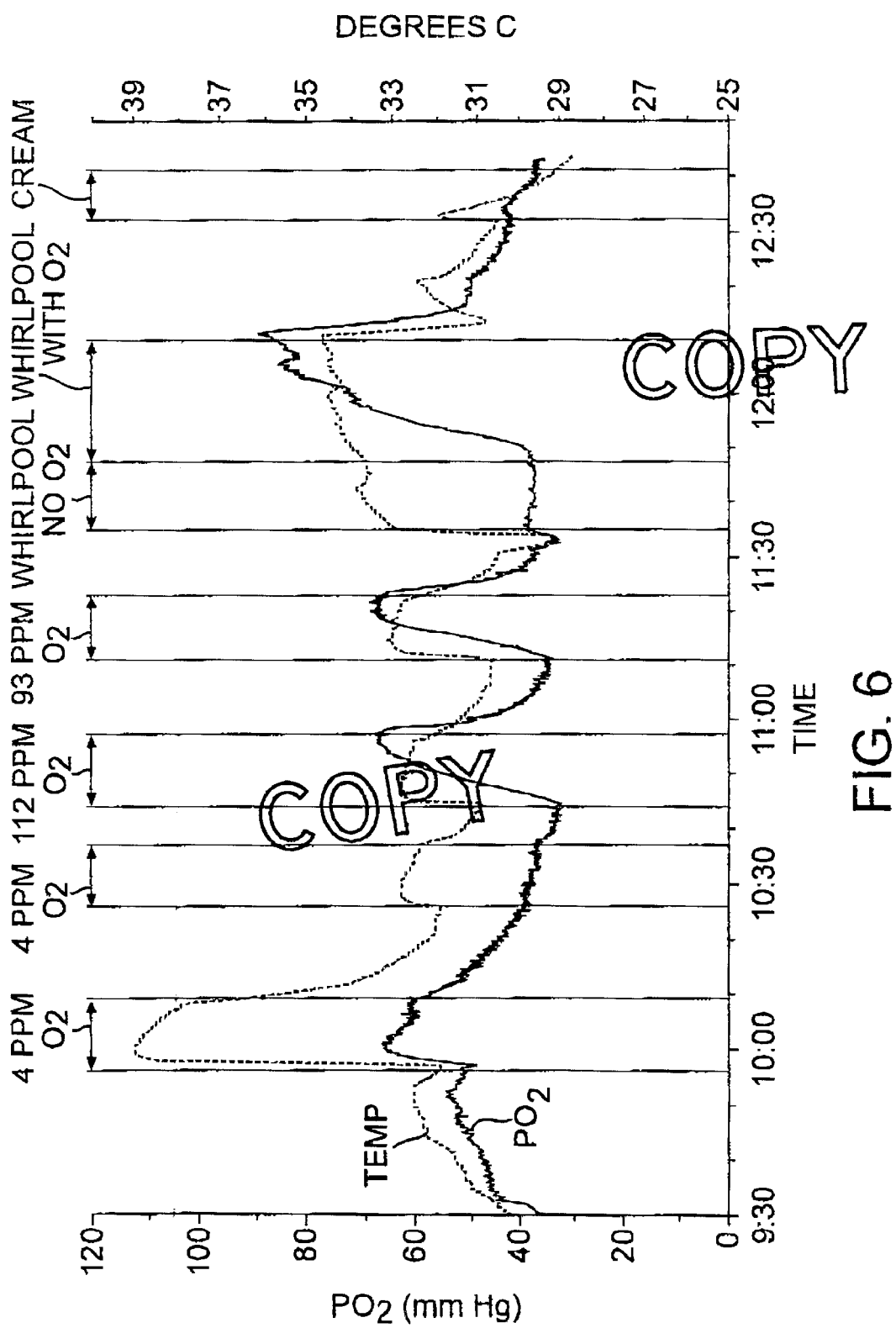
FIG. 6 Shows percent increases from baseline subcutaneous $pO_2$ in human subjects during control and oxygenation periods during immersion of tissue in a whirlpool bath.
Figure 7:
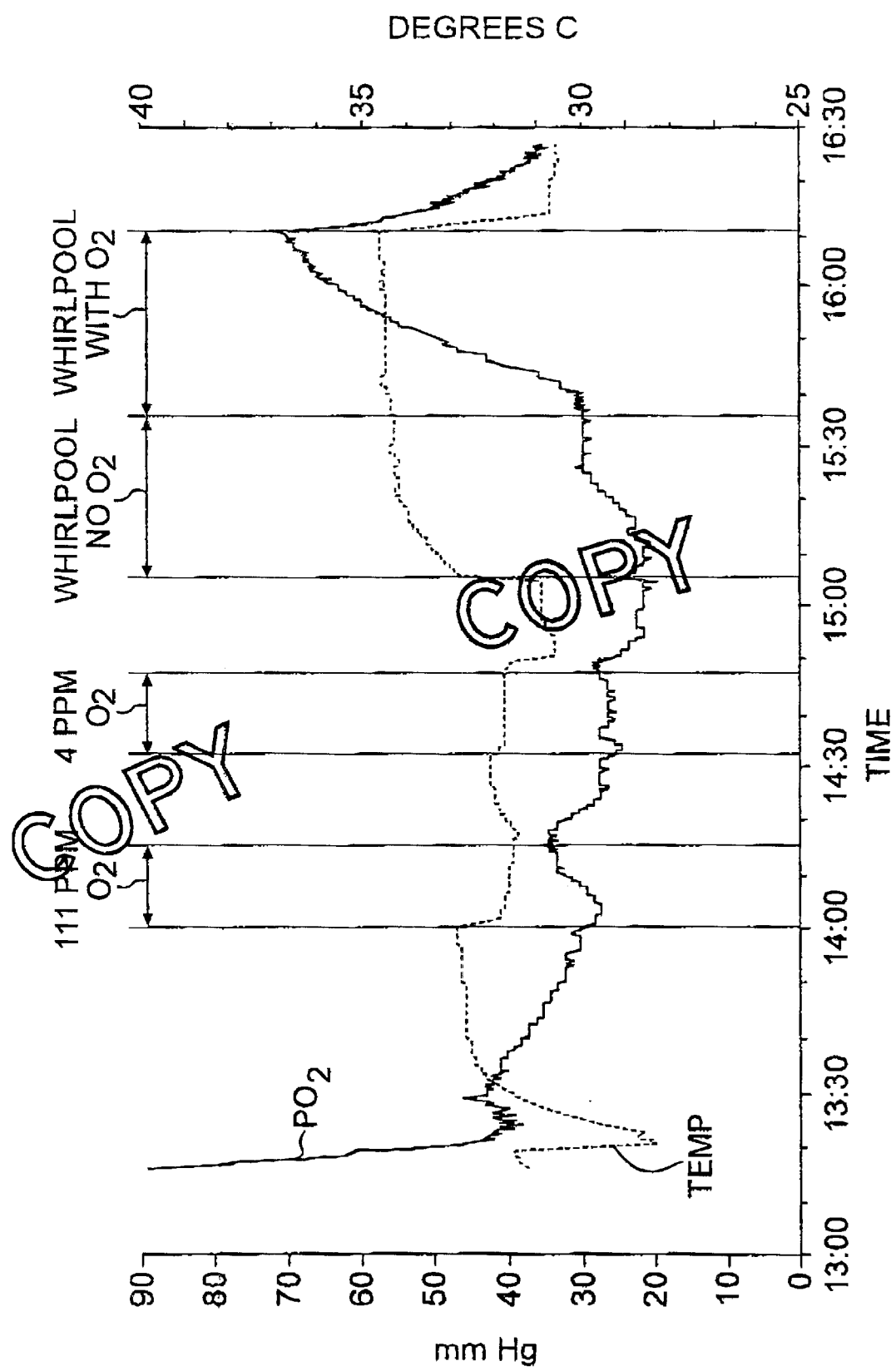
FIG. 7 Shows subcutaneous $pO_2$ increase overtime in subject HY01 during immersion of leg in a whirlpool bath.

Plots of temperature and subcutaneous $pO_2$ throughout the entire protocol for selected subjects are shown in FIG. 6 and FIG. 7.

TABLE 3

Sensor depth assessment and notes on specific subjects

| Subject | Sensor Depth | Notes |
|---|---|---|
| HY01 | could see bulge below skin | first test solution 39° C. |
| HY02 | Could not see below skin | sensor deep |
| HY03 | could see bulge below skin | reinserted sensor |
| HY04 | could feel sensor under skin | |
| HY05 | Could not feel, 2–3 mm deep | Ultrasound before whirlpool |
| HY06 | could feel sensor under skin, ~1.5 mm deep | Ultrasound before and after sensor placed |
| HY07 | could feel sensor under skin, ~1.5 mm deep | Ultrasound after sensor placed |
| HY08 | could feel sensor under skin | |
| HY09 | could feel sensor under skin | bleeding when put in catheter, blue line along sensor |
| HY10 | could feel sensor under skin | some bleeding observed on removal |

TABLE 4

Temperature and subcutaneous $pO_2$, pH, and $pCO_2$ for the whirlpool protocol

| Subject | $PO_2$ start | $PO_2$ cntrl | $PO_2$ wO2 | temp start | temp cntrl | temp wO2 | $PCO_2$ start | $PCO_2$ cntrl | $PCO_2$ wO2 | pH start | pH cntrl | pH wO2 |
|---|---|---|---|---|---|---|---|---|---|---|---|---|
| HY01 | 38 | 37 | 85 | 33 | 33.6 | 34.6 | 33.3 | 34.9 | 38.3 | 7.44 | 7.41 | 7.38 |
| HY02 | 22 | 18 | 31 | 31.4 | 33.1 | 35.7 | 32.1 | 34.3 | 38.7 | 7.47 | 7.46 | 7.42 |
| HY03 | 28 | 20 | 18 | 32.7 | 33 | 35.6 | 29.6 | 30.5 | 35.7 | 7.46 | 7.45 | 7.40 |
| HY04 | 21 | 20 | 27 | 32 | 32.1 | 33.4 | 41.5 | 42.7 | 46.5 | 7.41 | 7.40 | 7.38 |
| HY05 | 11 | 10 | 19 | 31.3 | 32.2 | 33.1 | 36.1 | 36.1 | 39.0 | 7.45 | 7.44 | 7.41 |
| HY06 | 40 | 40 | 49 | 32.3 | 32.5 | 34.1 | 34.3 | 34.2 | 36.2 | 7.46 | 7.45 | 7.43 |
| HY07 | 22 | 29 | 70 | 32.7 | 34.1 | 34.3 | 40.3 | 40.0 | 40.4 | 7.43 | 7.42 | 7.39 |
| HY08 | 28 | 24 | 32 | 35.1 | 35.2 | 35.4 | 41.4 | 44.1 | 46.8 | 7.40 | 7.37 | 7.35 |

TABLE 4-continued

Temperature and subcutaneous $pO_2$, pH, and $pCO_2$ for the whirlpool protocol

| Subject | $PO_2$ start | $PO_2$ cntrl | $PO_2$ wO2 | temp start | temp cntrl | temp wO2 | $PCO_2$ start | $PCO_2$ cntrl | $PCO_2$ wO2 | pH start | pH cntrl | pH wO2 |
|---|---|---|---|---|---|---|---|---|---|---|---|---|
| HY09 | 53 | 54 | 60 | 37 | 36.7 | 36.5 | 37.5 | 39.7 | 41.7 | 7.41 | 7.38 | 7.30 |
| HY10 | 42 | 42 | 47 | 34.1 | 34.2 | 34.4 | 33.8 | 34.4 | 35.7 | 7.46 | 7.45 | 7 |
| Mean | 31 | 29 | 44 | 33.2 | 33.7 | 34.7 | 36.0 | 37.1 | 39.9 | 7.44 | 7.42 | 7.39 |
| Std dev | 13 | 14 | 22 | 1.8 | 1.4 | 1.1 | 4.1 | 4.3 | 4.1 | 0.03 | 0.03 | 0.04 |

A summary of the whirlpool data for all subjects is shown in Table 4. The mean $pO_2$ for the 10 subjects started at 31+/−13 mm Hg, but was not significantly different at the end of the control period (29+/−14 mm Hg). After immersion in the oxygenated water, the subcutaneous $pO_2$ increased significantly to 44+/−22 mm Hg (p 0.026 compared to baseline and p 0.016 compared to the end of control). The percent increase (or decrease) in subcutaneous $pO_2$ during the control and oxygenation periods for each of the subjects is shown graphically in FIG. 8.

Figure 8:
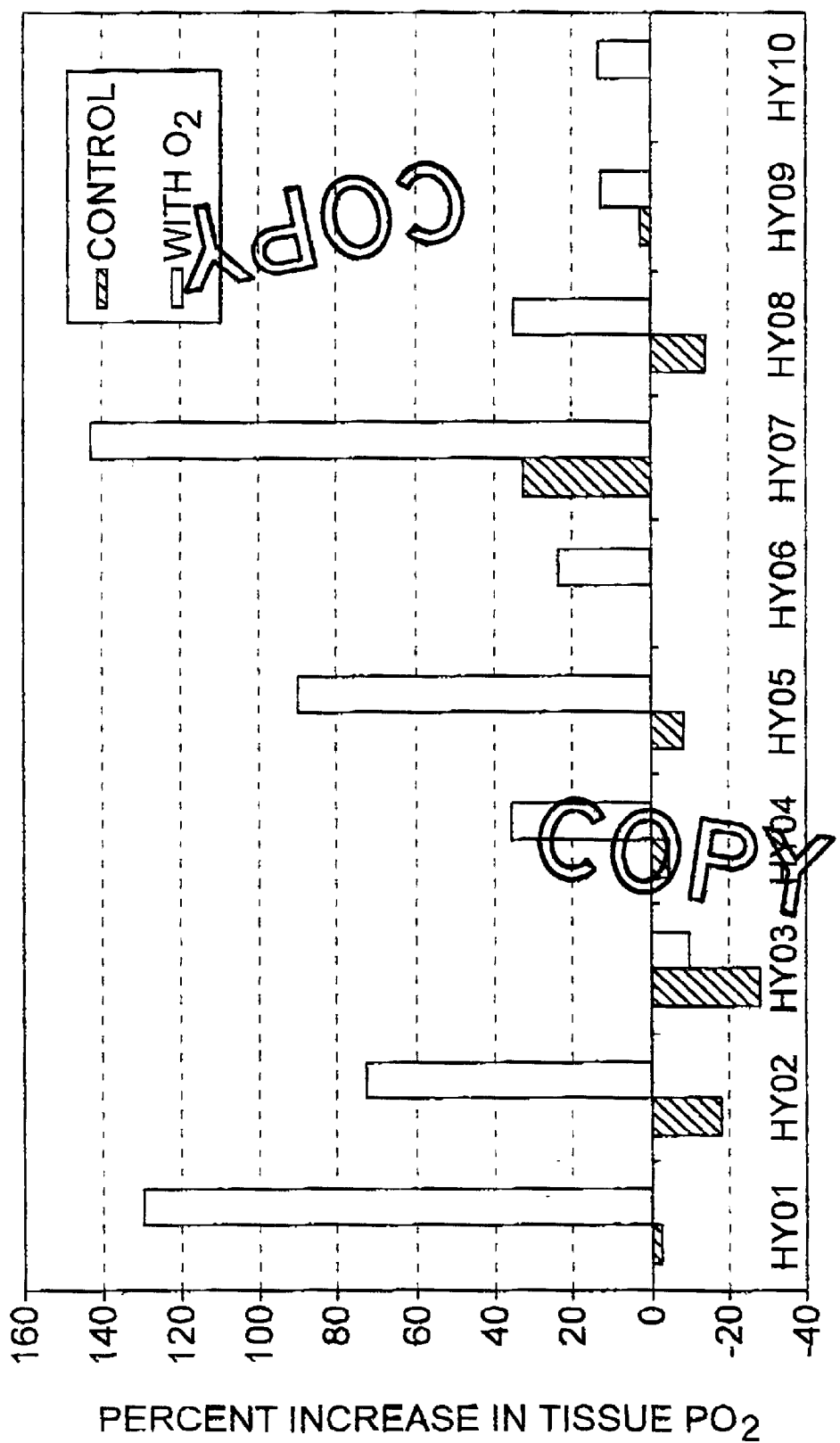
FIG. 8 Shows subcutaneous $pO_2$ increase overtime in a subject HY07 during immersion of leg in a whirlpool bath.

From FIG. 8 it can be seen that the percent increase in $pO_2$ varied considerably among the subjects, with 6 of the 10 showing increases in subcutaneous $pO_2$ of at least 30%. Significantly greater increases (141%, 130%, 90%, 70%) were observed for subjects HY07, HY01, HY05 and HY02, respectively. From Table 3 it can be seen that there is an increase in tissue temperature during both the control and oxygenation phases of the study. The temperature at the end of the oxygenation phase is significantly different from baseline (p 0.0006) and from the end of the control period (p 0.015). These temperature changes are accompanied by an increase in tissue $pCO_2$ and a decrease in tissue pH. Table 5 shows the average percent increase in baseline values for each of the parameters measured. In this analysis pH was converted to hydrogen ion concentration $[H^+]$.

TABLE 5

Average percent increase from baseline at the end of the control and oxygen periods

| | Average percent increase from baseline | |
|---|---|---|
| | Control | With O2 |
| Temperature | 2 | 5 |
| $P_{sc}O_2$ | −4 | 44 |
| $P_{sc}CO_2$ | 3 | 11 |
| $[H+]$ | 4 | 12 |

The data show that there is a significant increase in subcutaneous oxygen tension when the subject's leg is immersed in the oxygenated water, when compared to either baseline or control values in which the whirlpool contained regularly oxygenated (~4 ppm) water. Coincident with the subcutaneous $pO_2$ increase is an increase in temperature. The increase in temperature does not appear to affect the sensor response (which corrects for changes in temperature) but does have a number of physical and physiologic effects. As temperature increases, the solubility of oxygen in the blood decreases, increasing its release to the tissue. Also, temperature increases result in enhanced dissociation of oxygen from oxyhemoglobin. Lastly, increases in temperature result in vasodilation, which should bring more oxygen to the tissue. Nevertheless, for subjects HY01, HY05, HY07, HY08 and HY10, the increases in $pO_2$ seemed to be due to sources beyond those caused by a temperature rise, where for all subjects except HY01 the temperature rise was less than 1° C. It is possible however that the observed $pO_2$ increases may have been due to temperature in subjects HY02, HY04 and HY06 where the squared correlation coefficient ($R^2$) between $pO_2$ and temperature is above 0.8° C.

The levels of $pCO_2$ and $[H^+]$ increase during the period when the circulating water is being oxygenated. Both increase the same amount, which is not surprising given their dependence through the bicarbonate equilibrium. The source for these changes was not determined.

One subject (HY03) showed a decrease in $pO_2$ as a result of oxygenation. In this subject the sensor had to be reintroduced a second time. Injury to the tissue may have resulted in an impaired response to oxygen. A second subject (HY09) had obvious bleeding when the sensor was inserted and the sensor may have been insulated from the interstitial fluid by blood, dampening the response to the added oxygen. Some, though less, blood was observed when withdrawing the sensor from subject HY10 and may explain a small response from this subject as well. When the sensor is inserted in tissue, ample time must be allowed for temporary tissue injury to subside. Initially 30 minutes was believed to be acceptable, but continued decline after that period indicated that all injury was not resolved. Taking baseline readings at the beginning of the whirlpool period allowed at least 60 min stabilization for each subject. This time is consistent with studies conducted in Sweden using the Paratrend® sensor directly in subcutaneous tissue of swine (Mellstrom et al., 1999). The baseline values in those studies were not that different from those measured in this study: $pO_2$: 58+/−16; $pCO_2$: 42+/−5, and pH: 7.46+/−0.06. In a study of surgical patients where a polarographic oxygen electrode was used, baseline subcutaneous $pO_2$ was found to be 43+/−10 (Hopf et al., 1997). These reported values may be slightly different than values in these experiments because those sensors were probably placed deeper than the present ones, which were likely near the edge of the dermis.

Results showed that in at least half of the subjects there was a significant increase in tissue $pO_2$ related to the introduction of oxygen microbubbles in the whirlpool bath. The whirlpool was more effective than still oxygenated water (phase 1 of the test) in producing an increase in subcutaneous $pO_2$, despite the higher concentration of oxygen in the water used in the flexible bags (101–150 ppm $O_2$ vs. 55 ppm in the whirlpool). In the two subjects where there was a very good response in the whirlpool (HY01 and HY07) there was also a measurable response to oxygenated water in the bags. These were the only two subjects where there was a response during the bag portion of the study. These results indicate that individual subjects may differ in the rate of diffusion of oxygen through their skin to the sensor.

Sensor depth was controlled between 1 and 3 mm beneath the surface of the skin. However in the three subjects examined with the ultrasound, the structure of the skin and the thickness of the epidermis were quite variable. If oxygen is diffusion limited, it may only get to a certain depth. Different subjects may differ in their ability to hydrate or in the permeability of their skin to gas. Nevertheless, the results of the study showed that the high partial pressure of oxygen in the oxygenated water permitted a high enough concentration of oxygen outside the skin to facilitate diffusion of oxygen through the skin of the majority of the healthy subjects. Furthermore, permeability of the skin would not be a problem for the treatment of open wounds.

5.3 Example 3

Application of Method of Tissue Superoxygenation to Wound Healing

Preliminary studies will be conducted in diabetic patients and compared to those performed in animal and normal human testing to determine the effect of superoxygenated microbubbles on the rate of healing when administered to the non-healing wounds of diabetic patients. Patients will be maintained under tightly-controlled environmental conditions. Additionally, the wound area will be analyzed and anaerobic bacteria identified according to studies performed at the Institute of Molecular Biology and Medicine at University of Scranton. According to that study, approximately 10–20% of diabetic foot wounds fail initial antibiotic treatment. It is generally believed that several bacterial species may be present in these types of wounds. Because some of these organisms cannot be easily cultured, proper identification is problematic and thus, appropriate treatment modalities cannot be applied. The report examined the bacterial flora present in a chronic diabetic foot wound that failed antibiotic treatment. A tissue sample was collected from the base of the wound and used for standard microbiological culturing. DNA from the sample was used to amplify bacterial 16 S rDNA gene sequences and prepare a library, the clones of which were sequenced. The culture-based method identified a single anaerobic species, *Bacteroides fragilis*, whereas the method employing rDNA sequencing identified *B. fragilis* as a dominant organism and *Pseudomonas* (Janthinobacterium) *mephitica* as a minor component. The results indicated that the rDNA sequencing approach can be an important tool in the identification of bacteria from wound (Redkar et al., 2000).

Experiments will be conducted in controlled randomized fashion by administering the compositions to the wound area in varying concentrations and forms with subsequent analysis of the bacteria present in untreated wounds and those treated with superoxygenated water.

5.4 Example 4

Tissue Superoxygenation in Treatment of Leg Ulcers

A clinical study was undertaken to investigate and compare specifically the aerobic and anaerobic microbiology of infected and noninfected leg ulcers. Leg ulcers, defined as infected on the basis of clinical signs, were swab sampled and tested for aerobic and anaerobic microorganisms using stringent isolation and identification techniques (Bowler et al., 1999).

In this study, 220 isolates were cultured from 44 infected leg ulcers, and 110 isolates were from 30 non-infected leg ulcers. Statistical analysis indicated a significantly greater mean number of anaerobic bacteria per infected ulcer (particularly Peptostreptococcus spp. and Prevotella spp.) in comparison with the noninfected ulcer group (2.5 vs. 1.3, respectively) ($P<0.05$). Also, anaerobes represented 49% of the total microbial composition in infected leg ulcers compared with 36% in non-infected leg ulcers (Bowler et al., 1999).

Based on the results of these studies, superoxygenated microbubble compositions will be used to test the effect of the oxygenation treatment on the distribution of aerobic and anaerobic microflora which exist in leg ulcers. An indication of the effectiveness of the composition in combating leg ulcers and other wound infections will be determined by noting the relative changes in distribution of the anaerobes and aerobes.

5.5 Example 5

Superoxygenated Ice

The following example demonstrates the ability of highly oxygenated ice to hold high levels of oxygen and release oxygen at high levels. Results indicated that ice can be made with highly oxygenated water and that both the ice and melt fluid contain high concentrations of oxygen compared with tap water and ice as controls.

Two bottles of super-oxygenated (SO) fluid were stored at $-15°$ C. A third bottle was chilled at $8°$ C. Control samples were ice from tap water and tap water chilled to $8°$ C. The superoxygenated fluids were stored for approximately 6 months in tightly capped bottles. Oxygen levels ranged from 107 to 123 ppm at the time of storage. The bottles were removed from storage and oxygen levels measured with a modified high range Oxygard Handy Mk II meter with a standard unit of measurement of parts per million. The meter measured the oxygen at the surface of the ice where the ice initially melted ((Ice reading). The melt water was also measured (melt reading). The same measurements were made for the control tap water and tap water ice. Samples at $8°$ C. were poured into an open container and oxygen levels measured directly. Results are shown in Table 6.

TABLE 6

Oxygen Levels in superoxygenated and tap water ice

| Sample | Frozen | melt | Stored at 0° C. |
|---|---|---|---|
| Superoxygenated water $-15°$ C. | 82 ppm | 56 ppm | — |
| Superoxygenated water 0° C. | — | — | 103 ppm |
| Tap water $-15°$ C. | 7 ppm | 7 ppm | — |
| Tap water 0° C. | — | — | 4 ppm |

6.0 REFERENCES

The following literature citations as well as those cited are incorporated in pertinent part by reference herein for the reasons cited in the above text:

Bowler, Philip G.; Davies, Barry J., The microbiology of infected and noninfected leg ulcers, *International Journal of Dermatology*, 38(8): 573–578, 2000.

Elden, Harry R.; Kalli, Ted, Hydrogen Peroxide Emulsions, *DCI Magazine*, 157(vc): 38, 40, 42, 44, 47, 1995.

FDA Medical Devices Advisory Committee Meeting of: General and Plastic Surgery Devices Panel Closed Session, Nov. 17, 1998.

Hopf H W, Hunt T K, West J M, et al. Wound tissue oxygen tension predicts the risk of wound infection in surgical patients. Physiology of wound healing. *Arch Surg* 132:997–1004, 1997.

Hunt T, Rabkin J, Jensen J A, et al. Tissue oximetry: an interim report. *World J Surg* 11:126-132, 1987.

Jonsson K, Jensen J A, Goodson W H, et al. Tissue oxygenation, anemia, and perfusion in relation to wound healing in surgical patients. *Ann Surg* 214:605–613, 1991.

Ladin, U.S. Pat. No. 5,792,090, 1998.

Loori, U.S. Pat. No. 5,154,697, 1992.

Loori, U.S. Pat. No. 5,801,291, 1989.

Mellstrom A, Hartmann M, Jedlinska B, et al. Effect of hyperoxia and hypoxia on subcutaneous tissue gases and pH. *Euro Surg Res* 31:333–339, 1999.

Moschella and Hurley. Chapter 4: Permeability in Dermatology. W. B. Saunders; 1992

Quay, U.S. Pat. No. 5,573,751, 1996.

Redkar R; Kalns J; Butler W: Krock L; McCleskey F; Salmen A; Piepmeier E Jr; Del Vecchio V, Identification of bacteria from a non-healing diabetic foot wound by 16 S rDNA sequencing, *Molecular and Cellular Probes*, 14(3): 163–169, 2000.

Scherson et al., U.S. Pat. No. 5,855,570, 1999.

Spears, et al., U.S. Pat. No. 6,248,087

Taylor et al., U.S. Pat. No. 5,766,490, 1998.

Tegner E and A. Bjomberg, Hydrogen Peroxide Cream for the Prevention of White Pressure Areas in UVA Sunbeds, *Acta Derm, Venerol. (Stockh)*, 70:75, 1990.

Trammell, U.S. Pat. No. 5,029,589, 1991.

Van Liew et al., U.S. Pat. No. 5,869,538, 1999.

Whitney J. D., Physiologic Effects of Tissue Oxygenation on Wound Healing, *Heart and Lung* 18: 466–474, 1989.

Zelenak et al., U.S. Pat. No. 5,814,222, 1998.

Zelenak nee Zoltai et al., U.S. Pat. No. 5,006,352, 1991.

All of the methods and compositions disclosed and claimed herein can be made and executed without undue experimentation in light of the present disclosure. While the compositions and methods of this invention have been described in terms of preferred embodiments, it will be apparent to those of skill in the art that variations may be applied to the methods and compositions, in the steps or in the sequence of steps of the method described herein and in the modification of the apparatus connected with the methods and compositions without departing from the concept, spirit and scope of the invention. More specifically, it will be apparent that certain agents which are both chemically and physiologically related may be added to, combined with or substituted for the agents described herein while the same or similar results would be achieved. All such similar substitutes and modifications apparent to those skilled in the art are deemed to be within the spirit, scope and concept of the invention as defined by the appended claims. Accordingly, the exclusive rights sought to be patented are as described in the claims below.

What is claimed is:

1. A superoxygenated composition for application to the external surface of a tissue, the composition being in a form selected from the group consisting of a solid, liquid, cream, paste, powder, ointment, lotion, gel and aerosol; and comprising a solvent selected from the group consisting of water, a perfluorocarbon, alcohol and glycol, containing oxygen at a concentration between 45 ppm and 220 ppm, the oxygen being in the form of microbubbles having a diameter between 0.6 and 8 microns, said oxygen being at a partial pressure effective to raise the subepithelial region of the tissue from about 30% to about 120% above baseline $pO_2$.

2. The superoxygenated composition of claim 1, wherein the solvent contains oxygen at a concentration between 55 ppm and 220 ppm.

3. The superoxygenated composition of claim 1, wherein the solvent is water.

4. The superoxygenated composition of claim 1, wherein the solvent is selected from the group consisting of a perfluorocarbons, an alcohol, and a glycol.

5. The superoxygenated composition the composition of claim 1, wherein the composition is comprised in a form selected from the group consisting of a cream, a paste, a powder, an ointment, a lotion, a gel, and an aerosol.

6. The superoxygenated composition of claim 1, wherein the composition is in solid form.

7. The superoxygenated composition of claim 1, wherein the temperature of the composition is between about −70° C. and about 0° C.

8. A method of increasing exposure of anaerobic bacteria to oxygen, comprising applying the superoxygenated composition of claim 1 to a skin lesion suspected of harboring anaerobic bacteria.

9. The method of claim 8, wherein the anaerobic bacteria are pathogenic.

10. The method of claim 8, wherein the anaerobic bacteria are comprised within gangrenous or ulcerated tissue.

11. The method of claim 8, wherein the anaerobic bacteria are comprised within a wound.

12. The method of claim 11, wherein the wound is a burn wound.

13. A kit for use in topically increasing tissue oxygenation, the kit comprising a sealed permeable flexible container containing the composition of claim 1; and instructions for applying said composition to the skin of a subject in need of increased tissue oxygenation.

14. The kit of claim 13, further comprising a whirlpool generating device.

15. The kit of claim 13, further comprising a thermostat/heating device for adjusting temperature inside the container.

16. A method for reducing scar tissue comprising treating the scar tissue surface with the composition of claim 1.

17. A method of increasing tissue oxygenation in a mammal, comprising applying the superoxygenated composition of claim 1 to the external surface of a tissue for a time sufficient to increase the partial oxygen pressure of a subepithelial region of the tissue from about 30% to about 120% above baseline $pO_2$.

18. The method of claim 17, wherein the mammal is a human.

19. The method of claim 17, wherein the tissue is skin.

20. The method of claim 17, wherein the tissue is affected by a condition or disease.

21. The method of claim 20, wherein the condition is selected from the group consisting of a bedsore, a wound, a burn, and an ulcer.

22. The method of claim 20, wherein the disease is a bacterial infection.

23. The method of claim 22, wherein the bacterial infection is identified as an anaerobic pathogen bacterial infection.

24. The method of claim 17, wherein the applying is to an oral or vaginal mucosal surface, surface of lung tissue, or an organ for transplant.

25. The method of claim 17, wherein the superoxygenated composition is at about 0° C. to about 34° C.

26. The method of claim 17, wherein the superoxygenated composition comprises a pharmaceutically acceptable vehicle.

27. The method of claim 17, wherein the superoxygenated composition comprises water.

28. The method of claim 17, wherein the superoxygenated composition is applied under agitation.

29. The method of claim 28, wherein the agitation is provided in a whirlpool bath.

30. The method of claim 17, wherein the composition is applied in a cream, lotion or gel.

31. The method of claim 17, wherein the composition is applied by soaking, immersion, spraying, rubbing or aerosols.

* * * * *